(12) United States Patent
Cai et al.

(10) Patent No.: US 11,540,848 B2
(45) Date of Patent: Jan. 3, 2023

(54) ULTRASONIC THROMBUS REMOVING SYSTEM

(71) Applicant: JIANGXI UNIVERSITY OF SCIENCE AND TECHNOLOGY, Ganzhou (CN)

(72) Inventors: Gaipin Cai, Ganzhou (CN); Xiaoyan Luo, Ganzhou (CN); Pengfei Zhan, Ganzhou (CN); Tiedong Cheng, Ganzhou (CN); Haohua Chen, Ganzhou (CN); Huiming Chen, Ganzhou (CN)

(73) Assignee: JIANGXI UNIVERSITY OF SCIENCE AND TECHNOLOGY, Ganzhou (CN)

( * ) Notice: Subject to any disclaimer, the term of this patent is extended or adjusted under 35 U.S.C. 154(b) by 705 days.

(21) Appl. No.: 16/490,819

(22) PCT Filed: Aug. 24, 2018

(86) PCT No.: PCT/CN2018/102300
§ 371 (c)(1),
(2) Date: Sep. 3, 2019

(87) PCT Pub. No.: WO2019/037783
PCT Pub. Date: Feb. 28, 2019

(65) Prior Publication Data
US 2019/0388109 A1    Dec. 26, 2019

(30) Foreign Application Priority Data
Aug. 25, 2017   (CN) .......................... 201710741614.9

(51) Int. Cl.
*A61B 17/22* (2006.01)
*A61B 17/221* (2006.01)

(52) U.S. Cl.
CPC ...... *A61B 17/22004* (2013.01); *A61B 17/221* (2013.01); *A61B 2017/22054* (2013.01);
(Continued)

(58) Field of Classification Search
CPC ............ A61B 17/22004; A61B 17/221; A61B 2017/22054; A61B 2017/22067;
(Continued)

(56) References Cited

U.S. PATENT DOCUMENTS 6,398,792 B1    6/2002  O'Connor
10,874,423 B2 *  12/2020  Tada .............. A61B 17/320758
(Continued)

FOREIGN PATENT DOCUMENTS

CN    2689901 Y    4/2005
CN    1771880 A    5/2006
(Continued)

*Primary Examiner* — Quango Thanh
*Assistant Examiner* — Rachel O'Connell
(74) *Attorney, Agent, or Firm* — WPAT, PC

(57) ABSTRACT

An ultrasonic thrombus removing system includes a front sheath tube (1) and a rear sheath tube (5) that are independent and that are inserted into a blood vessel (2); a rear end outer portion of the front sheath tube (1) is mounted with a front blocking balloon (105), and a front end outer portion of the rear sheath tube (5) is mounted with a rear blocking balloon (504); a breaking cavity (4) being formed between the two blocking balloons; the front blocking balloon (105) and the rear blocking balloon (504) expand or contract in the blood vessel (2) by means of the squeezing or loosening of an external force so as to block or open front and rear sides of the thrombus (3); an inner portion of the rear sheath tube (5) is provided with a core tube (502) that co-axially penetrates therethrough, a front end of the core tube (502).

13 Claims, 5 Drawing Sheets

(52) U.S. Cl.
CPC ............... *A61B 2017/22067* (2013.01); *A61B 2017/22079* (2013.01)

(58) Field of Classification Search
CPC ........... A61B 2017/22079; A61B 8/12; A61M 2025/109; A61M 25/00; A61F 9/00745; A61C 1/07
See application file for complete search history.

(56) References Cited

U.S. PATENT DOCUMENTS

| | | | |
|---|---|---|---|
| 2004/0204670 A1 | 10/2004 | Nita et al. | |
| 2011/0160624 A1* | 6/2011 | Babaev | A61N 7/00 601/2 |
| 2014/0046244 A1 | 2/2014 | Ray et al. | |
| 2014/0142598 A1* | 5/2014 | Fulton, III | A61B 17/320725 606/159 |
| 2015/0306361 A1* | 10/2015 | Feig | A61B 17/22032 604/509 |
| 2016/0183967 A1* | 6/2016 | McGuckin, Jr. | A61B 17/320758 606/159 |
| 2016/0287277 A1* | 10/2016 | Du | A61B 17/22012 |
| 2017/0181760 A1* | 6/2017 | Look | A61M 1/84 |
| 2017/0189654 A1* | 7/2017 | Schwartz | A61B 5/0215 |

FOREIGN PATENT DOCUMENTS

| | | |
|---|---|---|
| CN | 101912289 A | 12/2010 |
| CN | 107348990 A | 11/2011 |
| CN | 102335022 A | 2/2012 |
| CN | 102512206 A | 6/2012 |
| CN | 102743207 A | 10/2012 |
| CN | 103767760 A | 5/2014 |
| CN | 104622538 A | 5/2015 |
| CN | 107397575 A | 11/2017 |
| CN | 107510491 A | 12/2017 |

* cited by examiner

ULTRASONIC THROMBUS REMOVING SYSTEM

FIELD OF THE INVENTION

The present invention belongs to a medical appliance used in interventional operations, which is an instrument for breaking, extracting, and discharging deposits in blood vessels; particularly, the present invention relates to an ultrasonic thrombus removing system.

BACKGROUND OF THE INVENTION

Thrombi are often formed in the cerebral arteries and veins of a human body. At present, drug-induced thrombolysis, surgical thrombus removing and mechanical thrombus removing are the main treatment methods for thrombosis.

Drug-induced thrombolysis is to dissolve thrombi directly or indirectly by intravenous injection of thrombolytic drugs, so as to dredge blocked blood vessels; another thrombolysis method is to introduce thrombolytic drugs directly to the thrombus sites through a catheter. Such a thrombolysis method is prone to induce a hemorrhage side effect. Hence, thrombolysis treatment is contraindicated especially for patients with a visceral or cerebral hemorrhage risk.

Surgical thrombus removing is to open an incision at the site of thrombus and remove the thrombus through the incision. However, it is difficult to remove the thrombus from the vein in surgical thrombus removing, and the residual thrombus debris generated during the operation may enter the lungs and cause pulmonary embolism.

Mechanical interventional thrombus removing is to introduce a thrombus removing device into the vein through a minimally invasive surgery, utilize angiography and x-ray fluoroscopy to control the thrombus removing device to come in contact with the thrombus, and directly break and remove the thrombus or penetrate through and remove the thrombus. Compared with thrombolysis and surgical thrombus removing, this method causes less trauma and has less impact on the vein where the thrombus deposits.

Patents related with mechanical thrombus removing mainly include the following ones: the Chinese Patent Document No. 201110098919.5 titled as Thrombus Breaking and Taking Device has discloses a thrombus removing device that can enter into the blood vessels of a human body and break and effectively remove a thrombus. The patent has solved a problem that the tiny guide wire is easy to bend when it penetrates through the thrombus, is difficult to penetrate through the thrombus at the center of the thrombus, and may cause damages to the blood vessel easily, and thereby improves the safety of thrombus removing. However, it is difficult to capture and discharge all the fragments of the thrombus from the body in the process that the guide wire penetrates through the thrombus and the metal mesh breaks the thrombus.

The Chinese Patent Document No. 200420049312.3 titled as Thrombus Breaking Device has disclosed a thrombus breaking device, which belongs to the field of medical apparatuses, and converts acoustic energy into mechanical energy and breaks a thrombus by vibration to attain a purpose of assisting thrombus removing. However, the device disclosed in the patent only provides in vitro treatment assistance in the thrombus removing process, because the device may cause tiny fragments of thrombus easily in the thrombus breaking or removing process, and those tiny fragments of thrombus are difficult to capture, and consequently are left in the venous blood and enter into the veins/arteries and viscera along the path, resulting in embolism or dysfunction of other veins and viscera.

The Chinese Patent Document No. 201010262495.7 titled as Thrombus Removing and Preparation Method and Application Method Thereof has disclosed a thrombus removing device, which comprises a conveying catheter, a guide wire rod, a guide wire head, and distal/proximal baskets, etc. In use, the thrombus removing device and the baskets are inserted into the blood vessel by means of X-ray, the baskets are released and opened after the thrombus removing device and the baskets penetrate through the thrombus, so that the thrombus is removed and loosened, and then is washed by the blood flow into the baskets and collected there. Since the thrombus is broken as the thrombus removing device and the baskets penetrate through the thrombus, the thrombus fragments will flow through the baskets to the rear end of the blood vessel. Consequently, secondary embolism may occur easily at the distal end of the vessel; moreover, the baskets may injure the tunica intima of the blood vessel when they collect the thrombus.

The Chinese Patent Document No. 201010238525.0 titled as Local Occluding Thrombus Scraper has disclosed a device for occluding, breaking and scraping thrombus. During thrombus removing, two blocking balloons are opened after they penetrate through the thrombus, the thrombus between the balloons is broken and scraped off by a thrombus scraping wire ball, and then is discharged from the blood vessel. When the balloons penetrate through the thrombus, they may produce thrombus fragments, which may cause secondary embolism at the distal end of the blood vessel. In addition, the thrombus scraping wire ball may directly injure the tunica intima of the blood vessel.

The Chinese Patent Document No. 201510108393.2 titled as Thrombus Removing System has disclosed a mechanical thrombus removing device that comprises a thrombus removing unit, a balloon guide catheter and a conveying micro-catheter. During thrombus removing, a balloon is expanded to protect the proximal end of the thrombus, and then the thrombus removing unit in a contracted state penetrates through the thrombus and then is expanded; the thrombus is separated from the blood vessel by pulling the thrombus removing unit, and then is collected and discharged from the body. When the thrombus removing unit penetrates through the thrombus, it may produce thrombus fragments, which may cause secondary embolism at the distal end of the blood vessel. In addition, the movement of the thrombus removing unit may directly injure the tunica intima of the blood vessel.

The Chinese Patent Document No. 201110414195.0 titled as Intravenous Ultrasound-Based Ultrasonic Diagnosis and Photoacoustic Therapy Device and Therapeutic Method Thereof has disclosed a method that incorporates ultrasonic imaging technology and photoacoustic therapy technology. Through three-dimensional ultrasound imaging of blood vessels, the method can help to identify the shape of vascular wall, the size of lumen, and the size and distribution of blood clots and plaques in the cardiovascular system; and ablate thrombi and break plaques by controlling laser intensity, wavelength and pulse width. Owing to the fact that the sizes and positions of thrombi and plaques in the cardiovascular system are uncertain, it is difficult to remove small-size thrombi by laser thrombolysis and plaque breaking.

SUMMARY OF THE INVENTION

To overcome the drawbacks of drug-induced thrombolysis, surgical thrombus removing and mechanical interventional thrombus removing in the prior art and meet the practical demand, the present invention designs an ultrasonic thrombus removing system, which can effectively break a thrombus and discharge all thrombus fragments from the body, and thereby realizes efficient and safe thrombus removing.

To attain the object described above, the present invention employs the following technical scheme:

An ultrasonic thrombus removing system, comprising a front sheath tube and a rear sheath tube that are relatively independent and may be inserted into a blood vessel, wherein, a front blocking balloon is fitted outside the rear end of the front sheath tube, and a rear blocking balloon is fitted outside the front end of the rear sheath tube; the front blocking balloon and the rear blocking balloon are located at two sides of a thrombus in the blood vessel respectively, and a breaking cavity is formed between the two blocking balloons; the front blocking balloon and the rear blocking balloon expand or contract inside the blood vessel by means of the squeezing or loosening of an external force so as to block or open front and rear sides of the thrombus; a core tube is provided inside the rear sheath tube in a way that the core tube penetrates through the rear sheath tube coaxially, a breaker configured to break the thrombus is provided at the front end of the core tube, and a discharge tube communicated with the core tube is provided at the rear end of the rear sheath tube.

Preferably, both the front sheath tube and the rear sheath tube comprise an inner tube that is closed at both ends and is hollow inside and an outer tube fitted outside the inner tube, the front blocking balloon and the rear blocking balloon are respectively fitted outside their respective inner tubes, each of the outer tubes comprises a thrombus distal end outer tube and a thrombus proximal end outer tube, and both the front blocking balloon and the rear blocking balloon are fitted outside the inner tubes between the thrombus distal end outer tube and the thrombus proximal end outer tube; a balloon expansion/contraction nut is fitted at the thrombus distal end outer tube, an outer end of the balloon expansion/contraction nut is statically connected with the inner tube, and an inner end of the balloon expansion/contraction nut is fitted with the thrombus distal end outer tube by threads; the front blocking balloon contracts or expands as it is axially compressed or released by the thrombus distal end outer tube.

Preferably, the two ends of the front blocking balloon are respectively fixedly connected with the thrombus distal end outer tube and the thrombus proximal end outer tube of the front sheath tube, and the two ends of the rear blocking balloon are respectively fixedly connected with the thrombus proximal end outer tube and the thrombus distal end outer tube of the rear sheath tube; frames of the front blocking balloon and the rear blocking balloon are mesh frames that are woven from elastic metal wires, the mesh frame is covered with a closed elastic film.

Preferably, radial clearance is arranged between the core tube and the inner wall of the rear sheath tube, several groups of convex ribs are distributed in the inner tube of the rear sheath tube, each group of convex ribs comprises three or more convex ribs that are evenly distributed on the inner cylindrical surface of the inner tube and parallel to the axis of the inner tube; the through-flow area formed by the convex ribs, the outer cylindrical surface of the core tube, and the inner cylindrical surface of the inner tube is no smaller than the through-flow area of the core tube.

Preferably, the ultrasonic thrombus removing system comprises a liquid supply system configured to supply a thrombus breaking medium to the breaker and an ultrasonic excitation system configured to make the thrombus breaking medium supplied by the liquid supply system form a high-speed pulsed jet stream.

Preferably, the ultrasonic thrombus removing system comprises a thrombus crushing medium supply tube, wherein the ultrasonic excitation system comprises an ultrasonic generator, an ultrasonic transducer, a horn, and an oscillation cavity that are sequentially connected, an inlet of the oscillation cavity is connected with the liquid supply system, an outlet of the oscillation cavity is connected with the thrombus breaking medium supply tube, and the thrombus crushing medium supply tube is connected with the core tube.

Preferably, the oscillation cavity is a cavity with a variable cross section, and is composed of a big cylindrical section, a first conical reduced section, a second conical reduced section, a small cylindrical hole section, and a horn nozzle which are arranged successively from the inlet end to the outlet end of the oscillation cavity, several groups of small through-holes are distributed in the wall surface of the cavity of the big cylindrical section, each group of small through-holes is evenly distributed in the circumferential direction of the big cylindrical section, the axes of the small through-holes are in a spatial helix tangent to the inner cylindrical surface of the upper oscillation cavity, with a helix angle $\beta$ is 0-90°; the generatrix of the second conical reduced section is an arc curve; the axial length of the small cylindrical hole section is greater than that of the second conical reduced section and the horn nozzle, and the axial length of the horn nozzle is smaller than that of the first conical reduced section.

Preferably, the horn is a unidirectional variable diameter shaft, which comprises a big cylindrical section, a conical reduced section and a small cylindrical section that are arranged sequentially from outside to inside; the generatrix of the conical reduced section is a logarithmic curve.

Preferably, the thrombus breaking medium is pulsed water, the outlet of the oscillation cavity is connected with a pulsed water supply tube, the pulsed water supply tube is connected with the core tube, a plurality of jet holes distributed in a front end wall of the core tube are arranged at the front end of the core tube, and the plurality of jet holes form the breaker, the pulsed water is jetted through the breaker to break the thrombus.

Preferably, the plurality of jet holes are arranged in the wall surface of the core tube in a way that straight holes and inclined holes are arranged in separate layers in circumferences, the axes of the straight holes are perpendicular to the wall surface of the core tube, the axes of the inclined holes and the axis of the core tube form an included angle $\alpha$ which is 0-90°, the jet holes are distributed in the wall surface of the core tube at 1-20 mm distance from the front end of the core tube, and altogether 8-20 layers of jet holes are provided.

Preferably, the liquid supply system comprises a liquid supply pump and a pressure/flow controller, wherein the liquid supply pump is connected with the input end of the pressure/flow controller.

Preferably, the ultrasonic thrombus removing system comprises a suction system, which comprises a suction pump and a thrombus fragment suction control device connected with the discharge tube through a communicating tube.

Preferably, the ultrasonic thrombus removing system comprises a thrombus breaking monitoring and control device, a breaking zone pressure monitoring device, and a X-ray probe arranged outside the breaking cavity, wherein the thrombus breaking monitoring and control device is connected with the X-ray probe, the breaking zone pressure monitoring device is a micro-pressure sensor, and the breaking zone pressure monitoring device is connected between the pressure/flow controller and a valve body of the oscillation cavity.

Preferably, the ultrasonic thrombus removing system comprises a thrombus removing control CPU connected with the ultrasonic generator, the thrombus fragment suction control device, the pressure/flow controller, the thrombus breaking monitoring and control device, and the breaking zone pressure monitoring device respectively.

The present invention attains the following beneficial effects:

(1) Utilizing the structure with a front sheath tube, a rear sheath tube, and two blocking balloons, the two ends of the thrombus are occluded, and then the thrombus is broken by means of a breaker, and the broken thrombus is discharged through a discharge tube; the system in the present invention has a novel structure and attains a good thrombus removing effect;

(2) By designing the rear sheath tube into a multi-layer nested structure, the rear sheath tube not only has a channel for conveying a high-pressure pulsed liquid medium to the breaking zone, but also has a channel for pumping and discharging the broken thrombus from the body;

(3) By effectively combining a wire mesh with an elastic film and designing the structure into an ellipsoidal balloon that can expand and contract, and fixedly connecting the balloon with the front sheath tube and the rear sheath tube respectively, a closed breaking zone for breaking the thrombus can be formed, and thereby the proximal end and the distal end are protected;

(4) By combining high-pressure jet technology with ultrasonic excitation technology, vibration of the liquid medium at a high frequency in a small amplitude can be produced, and a high-energy pulsed jet stream can be generated to cut the thrombus; such a pulsed jet stream can break the thrombus into super-fine fragments safely and efficiently; in addition, the working pressure, flow rate, vibration frequency and amplitude of the pulsed liquid medium can be determined according to the mechanical properties of the thrombus; the ultrasound vibration system comprising an ultrasonic generator, an ultrasonic transducer and an oscillator can cause ultrasonic vibration of the high-pressure water; such a pulsed jet stream can break the thrombus extensively and quickly;

(5) A horn in a logarithmic curve shape, an oscillation cavity structure with pulsed jet stream input holes distributed symmetrically at multiple points along the height and circumferential directions, and jet flow output holes in variable-diameter structures attaining a secondary acceleration effect are employed;

(6) A liquid supply system comprising a liquid supply pump and a pressure/flow controller is designed according to the requirement for the thrombus breaking force; in addition, the liquid supply system is connected with the oscillator of the ultrasonic vibration system for thrombus breaking to realize continuous supply of high-pressure water;

(7) A broken thrombus suction system comprising a suction pump and a thrombus discharging control system is designed according to the granularity of the broken thrombus and the pressure and flow rate of the liquid supply system, to suck and discharge the broken thrombus from the body;

(8) A sensing, detection and control system comprising a pressure sensor, an X-ray probe, a breaking zone pressure monitoring device, and a broken thrombus granularity monitoring device is designed according to the operating requirement of ultrasonic thrombus removing, to control the working parameters of the ultrasonic vibration system for thrombus breaking, the liquid supply system, and the broken thrombus suction system.

DESCRIPTION OF REFERENCE NUMBERS

1—front sheath tube; 101—inner tube of the front sheath tube; 102—ring; 103—balloon expansion/contraction nut; 104—thrombus distal end outer tube of the front sheath tube; 105—front blocking balloon; 106—thrombus proximal end outer tube of the front sheath tube; 2—blood vessel; 3—thrombus; 4—breaking cavity; 5—rear sheath tube; 501—breaker; 502—core tube; 503—thrombus proximal end outer tube of the rear sheath tube; 504—rear blocking balloon; 505—thrombus distal end outer tube of the rear sheath tube; 506—balloon expansion/contraction nut; 507—ring; 508—inner tube of the rear sheath tube; 509—small nut; 510—ring; 511—discharge tube; 512—jet hole; 513—convex rib; 6—pulsed water supply tube; 7—liquid supply system; 701—liquid supply pump; 702—pressure/flow controller; 8—ultrasonic excitation system; 801—ultrasonic generator; 802—ultrasonic transducer; 803—horn; 8301—big cylindrical section; 8302—conical reduced section; 8303—small cylindrical section; 804—oscillation cavity; 8401—small through-hole; 8402—second conical reduced section; 8403—small cylindrical hole section; 8404—horn nozzle; 8405—first conical reduced section; 8406—big cylindrical section; 8407—valve body; 9—thrombus removing control CPU; 10—suction system; 1001—suction pump; 1002—thrombus fragment suction control device; 1003—communicating tube; 11—thrombus breaking monitoring and control device; 12—breaking zone pressure monitoring device; 13—X-ray probe; 14—mesh frame; 15—elastic film.

DETAILED DESCRIPTION OF THE EMBODIMENTS

Figure 1:
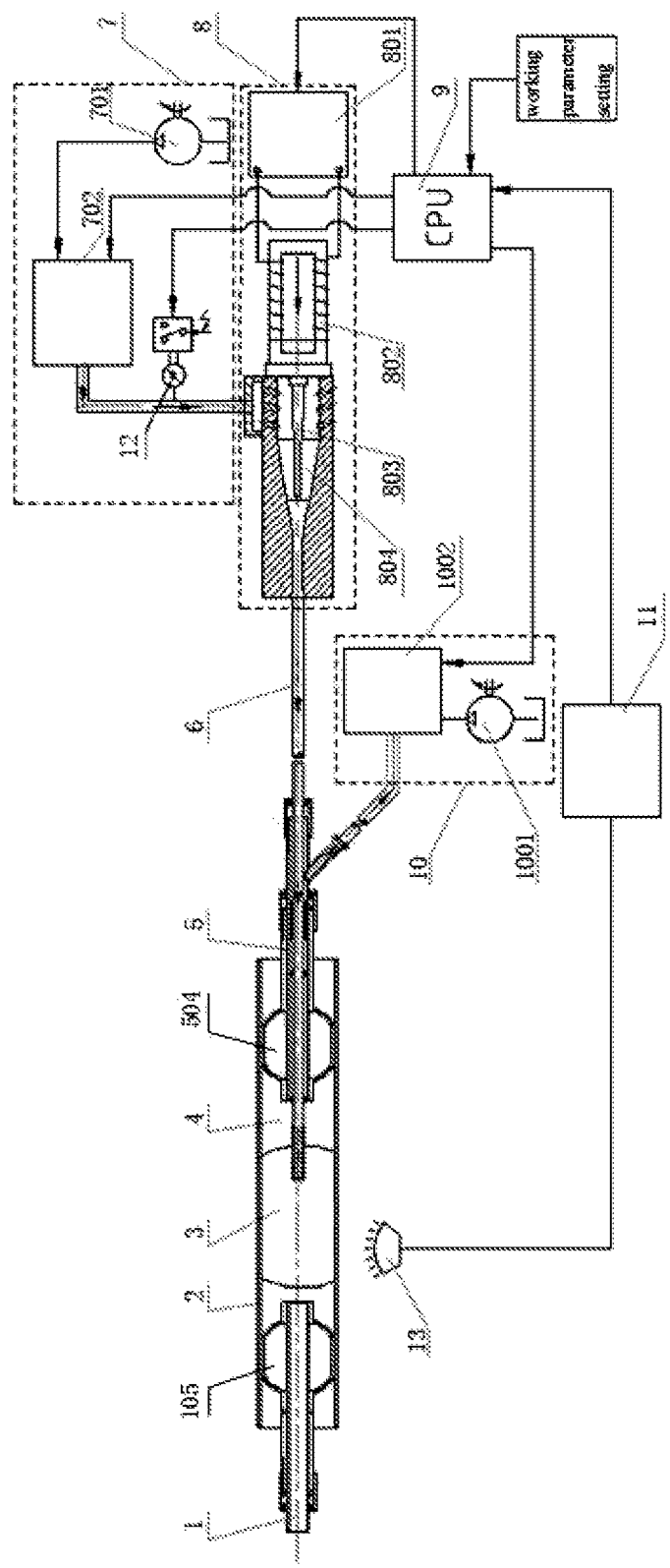
FIG. 1 is a schematic diagram of the overall structure of an embodiment of the ultrasonic thrombus removing system in the present invention.
Figure 2:
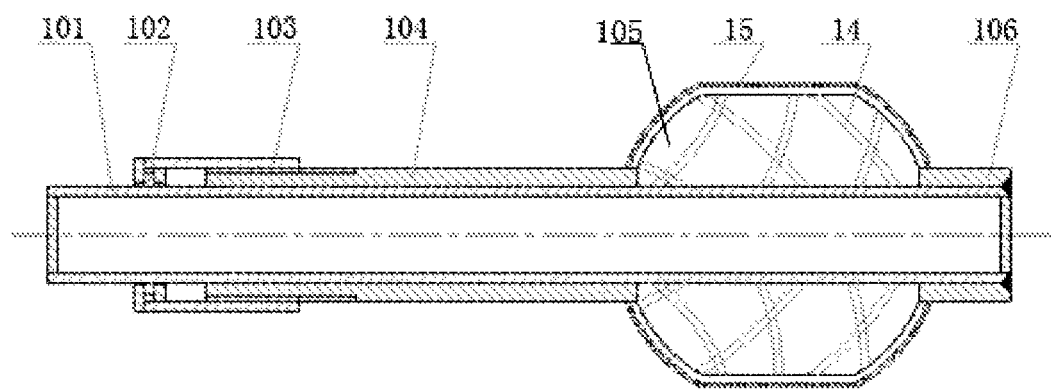
FIG. 2 is an enlarged schematic structural diagram of the front sheath tube.
Figure 3:
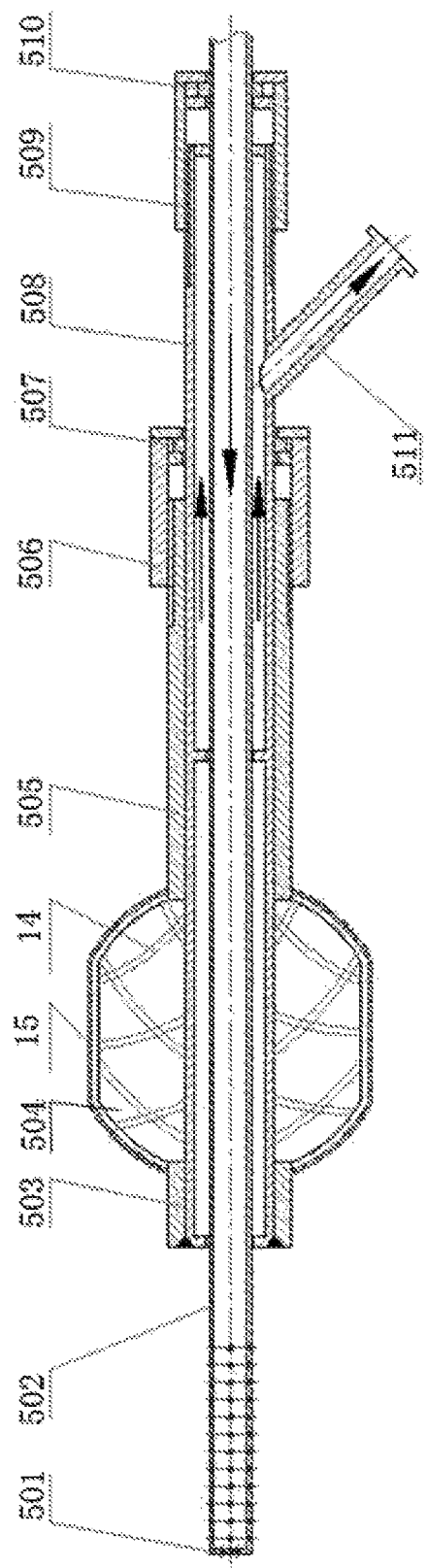
FIG. 3 is an enlarged schematic structural diagram of the rear sheath tube.
Figure 4:
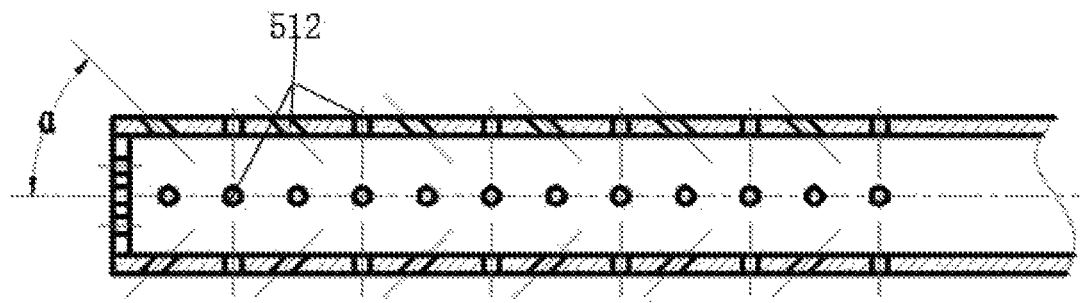
FIG. 4 is a partially enlarged schematic structural diagram of the breaker.
Figure 5:
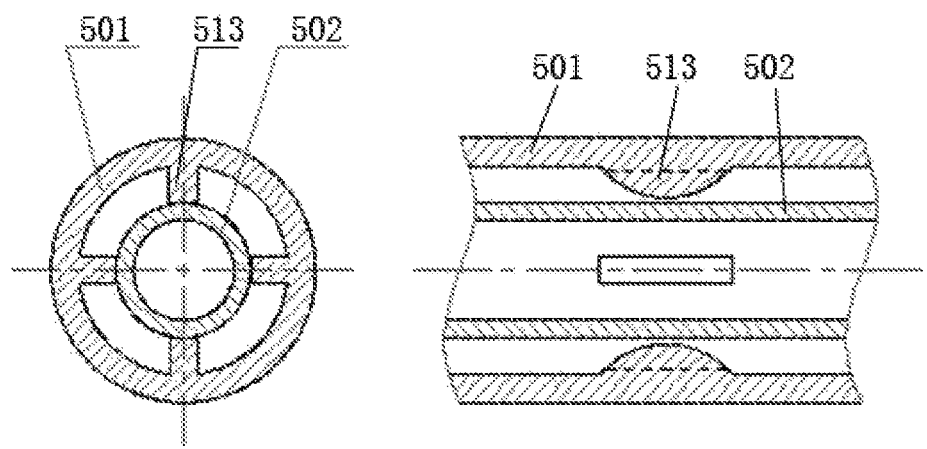
FIG. 5 is a partially enlarged sectional view illustrating the radial positions of the core tube and inner tube in the rear sheath tube.
Figure 6:
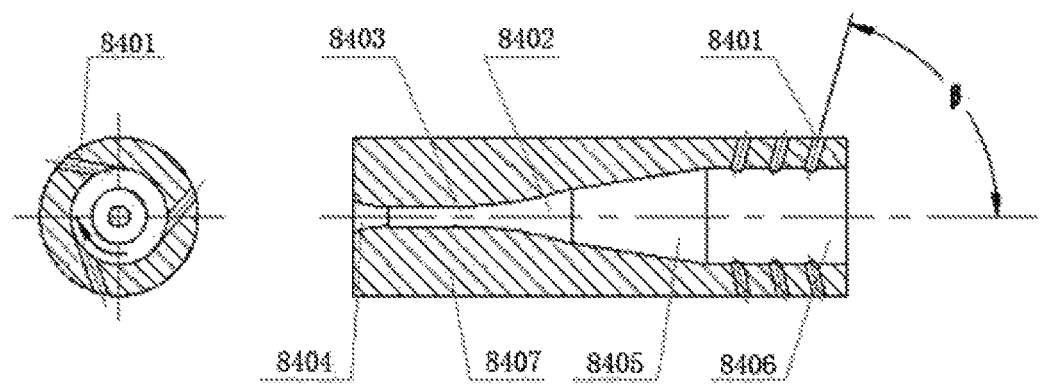
FIG. 6 is a schematic structural diagram of the oscillation cavity.
Figure 7:
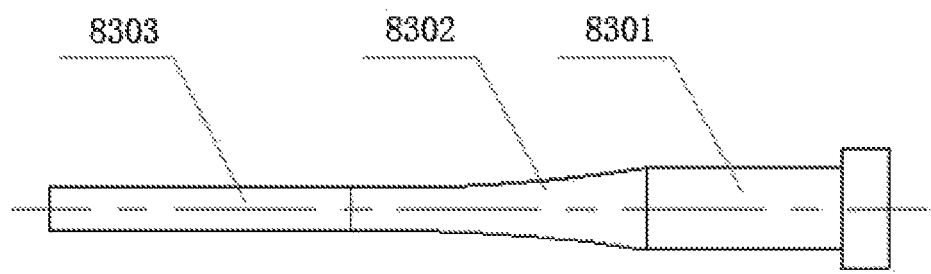
FIG. 7 is a schematic structural diagram of the horn.

Embodiments: Please See FIGS. 1-7.

The present invention discloses an ultrasonic thrombus removing system, which comprises a front sheath tube 1 and a rear sheath tube 5 that are relatively independent and may be inserted into a blood vessel 2, wherein, a front blocking balloon 105 is fitted outside the rear end of the front sheath tube 1, and a rear blocking balloon 504 is fitted outside the front end of the rear sheath tube 5; the front blocking balloon 105 and the rear blocking balloon 504 are located at two sides of a thrombus 3 in the blood vessel 2 respectively, and a breaking cavity 4 is formed between the two blocking balloons; the front blocking balloon 105 and the rear blocking balloon 504 expand or contract inside the blood vessel 2 by means of the squeezing or loosening of an external force so as to block or open front and rear sides of the thrombus 3; a core tube 502 is provided inside the rear sheath tube 5 in a way that the core tube 502 penetrates through the rear sheath tube 5 coaxially, a breaker 501 configured to break the thrombus is provided at the front end of the core tube 502, and a discharge tube 511 is provided at the rear end of the rear sheath tube 5 in a way that the discharge tube 511 communicates with the core tube 502.

The present invention belongs to a medical appliance used in interventional operations, which is an instrument for breaking, extracting, and discharging deposits in blood vessels.

After the site of the thrombus is detected, the front sheath tube 1 is inserted to the front end of the thrombus 3 in the blood vessel 2 first, and the front blocking balloon 105 expands to occlude the front end of the blood vessel 2 till it adheres to the inner wall of the blood vessel 2; then, the rear sheath tube 5 is inserted to the rear end of the thrombus 3, and the rear blocking balloon 504 expands till it adheres to the inner wall of the blood vessel 2; thus, the thrombus 3 is occluded between the two balloons, and the enclosed area is the breaking cavity 4. After the front sheath tube 1 and the rear sheath tube 5 are inserted into the blood vessel 2 and the occlusion of the thrombus 3 is completed, the thrombus is broken by the breaker 501, and the thrombus fragments are discharged through the discharge tube 511.

As a preferred embodiment as well as one of the features of the present invention, the ultrasonic thrombus removing system in the present invention further comprises an ultrasonic excitation system 8 and a thrombus crushing medium supply tube, wherein the ultrasonic excitation system 8 comprises an ultrasonic generator 801, an ultrasonic transducer 802, a horn 803, and an oscillation cavity 804 that are sequentially connected, an outlet of the oscillation cavity 804 is connected with the thrombus breaking medium supply tube, and the thrombus crushing medium supply tube is connected with the core tube 502.

The ultrasonic generator 801 is configured to generate ultrasonic waves, and the ultrasonic transducer 802 converts to inputted electric power into mechanical power (i.e., ultrasonic waves) and then transmits the mechanical power, while consuming a very small part of the power.

Preferably, the oscillation cavity 804 is a cavity with a variable cross section, and is composed of a big cylindrical section 8406, a first conical reduced section 8405, a second conical reduced section 8402, a small cylindrical hole section 8403, and a horn nozzle 8404, which are arranged successively from the inlet end to the outlet end of the oscillation cavity 804, several groups of small through-holes 8401 are distributed in the wall surface of the cavity of the big cylindrical section 8406, each group of small through-holes 8401 is evenly distributed in the circumferential direction of the big cylindrical section 8406, the axes of the small through-holes 8401 are in a spatial helix tangent to the inner cylindrical surface of the upper oscillation, with a helix angle β is 0-90°; the generatrix of the second conical reduced section 8402 is an arc curve; the axial length of the small cylindrical hole section 8403 is greater than that of the second conical reduced section 8402 and the horn nozzle 8404, and the axial length of the horn nozzle 8404 is smaller than that of the first conical reduced section 8405.

The horn 803 is a unidirectional variable diameter shaft, which comprises a big cylindrical section 8301, a conical reduced section 8302 and a small cylindrical section 8303 that are arranged sequentially from outside to inside; the generatrix of the conical reduced section 8302 is a logarithmic curve.

The horn is an important component of an ultrasonic excitation system. The main function of the horn in a vibration system is to amplify the displacement or velocity of the mass point involved in the mechanical vibration and concentrate the ultrasonic energy to a small area (e.g., energy concentration). Therefore, the horn is also referred to as an ultrasonic velocity transformer or ultrasonic energy concentrator. The horn 803 employs a variable-diameter structural design to improve the shape factor of the horn and increase the amplitude amplification coefficient of the horn. The structural shape of each section of the oscillation cavity is determined through tests and measurements according to the required magnitude of the displacement of the minimum end (tail end) of the horn on the basis of the force-displacement relationship of a member with a complex cross section.

Preferably, the thrombus breaking medium in the present invention is water. It is foreseeable that other media may be used as breaking media in replacement of water, such as air flow. The outlet of the oscillation cavity 804 is connected with a pulsated water supply tube 6, the pulsed water supply tube 6 is connected with the core tube 502, a plurality of jet holes 512 distributed in a front end wall of the core tube 502 are arranged at the front end of the core tube 502, and the plurality of jet holes 512 form the breaker 501, the pulsed water is jetted through the breaker 501 to break the thrombus.

Since the horn is arranged in the oscillation cavity, the horn vibrating at a high frequency will have an excitation effect on the liquid water when the liquid water flows through the oscillation cavity, so that the liquid water obtains alternating mechanical energy and becomes pulsed water. The pulsed water with alternating mechanical energy can cut and separate the thrombus.

The cross section of the oscillation cavity is reduced in the direction from the first conical reduced section 8405 to the second conical reduced section 8402, mainly for improving the flow velocity of the pulsed water under the condition of the same flow rate of the pulsed water, so that the pulsed water enters into the cylindrical holes of the small cylindrical hole section 8403 at an axial flow velocity higher than the flow velocity in the oscillation cavity; when the pulsed water passes through the horn nozzle 8404 that is a tapered hole at the leftmost end, a Laval effect is produced, i.e., the pulsed water is further accelerated and thereby obtains higher kinetic energy to facilitate thrombus breaking. The cross section of each section is determined according to the expected kinetic energy of the pulsed water.

After the pulsed water enters into the oscillation cavity at a certain helix angle, it forms a vortex field in the oscillation cavity, and thereby the pressure loss of the pulsed water resulted from reduced cross sectional area of the oscillation cavity is reduced; the helix angle shall be determined under a principle that the liquid water can not only form a vortex flow in the oscillation chamber but also achieve the fastest axial flow velocity. The helix angle β is 0-90°, usually within a range of 30°-60°, optimally is 45°.

The plurality of jet holes 512 are arranged in the wall surface of the core tube 502 in a way that straight holes and inclined holes are arranged in separate layers in circumferences, i.e., one layer of straight holes followed by one layer of inclined holes, and so on: the axes of the straight holes are perpendicular to the wall surface of the core tube, the axes of the inclined holes and the axis of the core tube form an included angle $\alpha$ which is 0-90°, the jet holes 512 are distributed in the wall surface of the core tube 502 at 1-20 mm distance from the front end of the core tube 502, and altogether 8-20 layers of jet holes 512 are provided.

With a structure of alternative arrangement of straight holes and inclined holes in layers, the thrombus can be impacted at different angles, and the water columns jetted in different directions form turbulent flows and can break the thrombus into small particles uniformly, so as to avoid thrombus particles in different sizes produced by water columns jetted in the same direction; otherwise thrombus particles in large sizes can't be broken further easily and discharged through the discharge tube 511.

As a preferred embodiment, both the front sheath tube 1 and the rear sheath tube 5 comprise an inner tube that is closed at both ends and is hollow; the front blocking balloon 105 and the rear blocking balloon 504 are fitted outside their respectively inner tubes; outer tubes are fitted outside the inner tube of the front sheath tube 1 and the inner tube of the rear sheath tube 5 in the present invention, wherein the inner tube 101 is the inner tube of the front sheath tube, and the inner tube 508 is the inner tube of the rear sheath tube; the outer tube comprises a thrombus distal end outer tube and a thrombus proximal end outer tube, the outer tubes 104 and 106 shown in the figures are the thrombus distal end outer tube and the thrombus proximal end outer tube of the front sheath tube 1 respectively, and the outer tubes 503 and 505 are the thrombus proximal end outer tube and the thrombus distal end outer tube of the rear sheath tube respectively. The front blocking balloon 105 and the rear blocking balloon 504 are fitted outside the inner tubes between the two outer tubes; balloon expansion/contraction nuts are fitted at the thrombus distal end outer tubes, and are represented by reference numbers 103 and 506 in the figures; the outer end of the balloon expansion/contraction nut is statically connected with the inner tube, and the inner end of the balloon expansion/contraction nut is fitted with the thrombus distal end outer tube by threads; the front blocking balloon 105 is compressed or released axially through the thrombus distal end outer tube to achieve contraction and expansion.

After the site of the thrombus is detected, the front sheath tube 1 is inserted to the front end of the thrombus 3 in the blood vessel 2 first, the balloon expansion/contraction nut 103 on the front sheath tube 1 is turned so that the thrombus distal end outer tube 104 of the front sheath tube 1 can moved toward the proximal end of the thrombus along the inner tube 101, and thereby the front blocking balloon 105 is expanded, till the front blocking balloon 105 supports the blood vessel 2 and adheres to the inner wall of the blood vessel 2, to realize protection of the proximal end; the rear sheath tube 5 is inserted to the rear end of the thrombus 3, the balloon expansion/contraction nut 506 on the rear sheath tube 5 is turned so that the thrombus distal end outer tube 505 of the rear sheath tube can move toward the proximal end of the thrombus along the inner tube 508 of the rear sheath tube, and thereby the rear blocking balloon 504 is expanded, till the rear blocking balloon 504 adheres to the inner wall of the blood vessel 2, to prevent fine thrombus fragments from flowing to the distal end; thus, the thrombus is occluded between the two balloons. After the front sheath tube 1 and the rear sheath tube 5 are inserted into the blood vessel 2 and the occlusion of the thrombus 3 is completed, the water supply system is opened, so that pulsed water flows through the breaker 501 via the pulsed water supply tube 6 and then is jetted through the jet holes 512 to break the thrombus 3; the fragments of the broken thrombus are sucked away by the suction system 10 and fully discharged through the discharge tube 511.

The two ends of the front blocking balloon 105 are respectively fixedly connected with the thrombus distal end outer tube 104 and the thrombus proximal end outer tube 106 of the front sheath tube 1, and the two ends of the rear blocking balloon 504 are respectively fixedly connected with the thrombus proximal end outer tube 503 and the thrombus distal end outer tube 505 of the rear sheath tube 5; frames of the front blocking balloon 105 and the rear blocking balloon 504 are mesh frames 14 that are woven from elastic metal wires, the mesh frame 14 is covered with a closed elastic film 15. The front blocking balloon and the rear blocking balloon have a meshed structure woven from elastic metal wires and are covered by an elastic film, so that the elastic film is in a slack state but the balloon is still a spherical frame structure when the balloon expansion/contraction nut is loosened up. When the front end and rear end of the thrombus are to be occluded, the balloon expansion/contraction nuts may be tightened up simply to squeeze the balloons to deform. Of course, the structure of the front blocking balloon and the rear blocking balloon is not limited to the structure described above. Instead, a simple inflatable structure may be used and the inflatable structure may be connected with the front blocking balloon and the rear blocking balloon so that they communicate with each other.

The outer ends of the balloon expansion/contraction nuts 103 and 506 are provided with an annular groove respectively, and the balloon expansion/contraction nuts are fixedly connected with their respective inner tubes via rings 102 and 510 arranged in the annular grooves; a small nut 509 is fitted outside the right end of the core tube 502, the outer end of the small nut 509 is also provided with an annular groove, and is fixedly connected with the core tube 502 via a ring 510 arranged in the annular groove, the other end of the small nut is fitted with the inner tube 508 of the rear sheath tube by threads; the balloon expansion/contraction nuts 103 and 506 and the small nut 509 are hollow cylindrical structures with a bottom, an annular groove is arranged on the bottom, the respective ring is embedded in the annular groove, and there is certain clearance between the ring and the annular groove. Radial clearance is arranged between the core tube 502 and the inner wall of the rear sheath tube 5, several groups of convex ribs 513 are distributed in the inner tube 508 of the rear sheath tube, each group of convex ribs comprises three or more convex ribs that are evenly distributed on the inner cylindrical surface of the inner tube 508 and parallel to the axis of the inner tube; the through-flow area formed by the convex ribs, the outer cylindrical surface of the core tube 502, and the inner cylindrical surface of the inner tube 508 is no smaller than the through-flow area of the core tube 502.

The ultrasonic thrombus removing system further comprises a liquid supply system 7, a thrombus removing control CPU 9, a suction system 10, a thrombus breaking monitoring and control device 11, a breaking zone pressure monitoring device 12, and an X-ray probe 13 arranged outside the breaking cavity 3; the liquid supply system 7 comprises a liquid supply pump 701 and a pressure/flow controller 702; the liquid supply pump 701 is connected with an input end of the pressure/flow controller 702; the suction system comprises a suction pump 1001 and a thrombus fragment suction control device 1002 connected with the discharge tube 511 through a communicating tube 1003; the thrombus removing control CPU 9 is connected with the ultrasonic generator 801, the thrombus fragment suction control device 1002, the pressure/flow controller 702, the thrombus breaking monitoring and control device 11, and the breaking zone pressure monitoring device 12 respectively; the thrombus breaking monitoring and control device 11 is connected with the X-ray probe 13 arranged outside the breaking cavity, the breaking zone pressure monitoring device 12 is a micro-pressure sensor, and the breaking zone pressure monitoring device 12 is connected between the pressure/flow controller 702 and a valve body 8407 of the oscillation cavity 804.

After the front sheath tube 1 and the rear sheath tube 5 are inserted into the blood vessel and the occlusion of the thrombus is completed, the ultrasonic excitation system 8, the liquid supply system 7, the suction system 10, and the thrombus breaking monitoring and control device 11 are started by means of the thrombus removing control CPU 9 respectively.

By turning the small nut 509 of the rear sheath tube 5, the core tube 502 can move toward the proximal end of the thrombus in the inner tube 508, and thereby move to the site of the thrombus 3; when the breaker 501 approaches the thrombus 3, the liquid supply system 7 supplies liquid to the breaker 501 at preset pressure and flow rate under the coordination of the thrombus removing control CPU; at the same time, the ultrasonic generator 801 generates 15-20 KHz high-frequency electric pulses, and makes the horn 803 vibrate mechanically at a high frequency in a small amplitude via the ultrasonic transducer 802. The mechanical vibration excites the high-pressure liquid medium in the oscillation cavity 804 to have resonance and turn into a 15-20 KHz pulsed jet stream, which is accelerated again through the discharge port of the oscillation cavity and enter into the tail end of core tube of the rear sheath tube 5 at a high speed, and then is jetted through the jet holes 512 of the breaker 501 to impact, cut, break, and separate the thrombus deposited in the blood vessel, so that the thrombus is turned into fine fragments and suspends in the liquid medium in the breaking cavity 4.

When the high-speed pulsed jet stream flows out from the breaker 501 and breaks the thrombus 3, the thrombus fragment suction control device 1002 of the suction system 10 is coordinated by the thrombus removing control CPU, and the flow rate of the supplied liquid is used as the working flow rate of the suction pump 1001; thus, the required liquid flow rate for breaking the thrombus is ensured and the fragments of the broken thrombus can be discharged from the blood vessel, and any vacuum area in the blood vessel can be avoided in the thrombus removing process.

An signal of actual pressure of the liquid medium in the thrombus breaking zone is acquired in real time by means of the micro-pressure sensor of the breaking zone pressure monitoring device 12 and transmitted to the thrombus removing control CPU via the micro-pressure sensor; the actual pressure is compared with a preset pressure parameter, and then a feedback signal is transmitted to the pressure/flow controller 702 in the liquid supply system 7 to adjust the output pressure of the liquid supply system; thus, the required pressure of the pulsed jet stream for thrombus breaking can be ensured, and pressure safety in the breaking zone can be guaranteed.

Image information on the position, size, and blockage of the thrombus 3 can be acquired before thrombus breaking by means of the X-ray probe 13 and a contrast medium; in the process of ultrasonic thrombus breaking, images on the size of particles of the broken thrombus and the thrombus clearing condition are acquired, and the image information is processed by the thrombus removing control CPU and then displayed. The thrombus removing process is carried out on the basis of the image information, till all thrombi or plaques in the blood vessel are removed and the blood vessel is unobstructed.

Compared with other thrombus removing devices, the thrombus removing system in the present invention has the following unique features: firstly, occluding thrombus removing is used, and the fragments of the broken thrombus can flow to the distal end of the blood vessel to avoid secondary embolism; secondly, ultrasonic excitation technology is utilized to obtain a liquid medium with high-frequency pulsed energy to break the thrombus into super-fine fragments, and thereby any blockage of the discharge tube by large thrombus fragments can be avoided; thirdly, by reasonably controlling the vibration intensity of the liquid medium, the thrombus can be effectively removed, and any direct injury to the tunica intima of the blood vessel caused by rigid components in contact with the tunica intima of the blood vessel can be effectively avoided; fourthly, the pressure of the thrombus breaking cavity, the granularity of the broken thrombus, and the flow rate and pressure of the liquid supply system and the discharge system can be monitored in real time by means of the sensing and detection system, so that the safety and effectiveness of the thrombus removing process can be ensured.

While the present invention has been illustrated and described with reference to some embodiments, the present invention is not limited to those specific embodiments. Any equivalent variation or any direct or indirect application of application implemented in other relevant technical fields on the basis of the disclosure in the specification and accompanying drawings of the present invention shall be deemed as falling into the patent protection scope of the present invention.

What is claimed is:

1. An ultrasonic thrombus removing system, comprising:
    a front sheath tube (1) and a rear sheath tube (5) are independently inserted into a blood vessel (2);
    a front blocking balloon (105) is fitted outside a rear end of the front sheath tube (1), and a rear blocking balloon (504) is fitted outside a front end of the rear sheath tube (5), wherein the front blocking balloon (105) and the rear blocking balloon (504) are configured to be placed at both sides of thrombus (3) within the blood vessel (2) respectively;
    a breaking cavity (4) formed between the two blocking balloons, wherein the front blocking balloon (105) and the rear blocking balloon (504) expand or contract within the blood vessel (2) by means of squeezing or loosening of an external force so as to block or open front and rear sides of the thrombus (3);
    a core tube (502) positioned inside the rear sheath tube (5) penetrating through the rear sheath tube (5) coaxially;
    a breaker (501), configured to break the thrombus (3), located at a front end of the core tube (502);
    a discharge tube (511), communicated with the core tube (502, located at a rear end of the rear sheath tube (5); and
    a liquid supply system (7) configured to supply a thrombus breaking medium to the breaker (501); and
    an ultrasonic excitation system (8) configured to make the thrombus breaking medium supplied by the liquid supply system (7) form a high-speed pulsed jet stream.

2. The ultrasonic thrombus removing system of claim 1, wherein, both the front sheath tube (1) and the rear sheath tube (5) comprise an inner tube that is closed at both ends and is hollow inside and an outer tube fitted outside the inner tube, the front blocking balloon (105) and the rear blocking balloon (504) are respectively fitted outside their respective inner tubes, each of the outer tubes comprises a thrombus distal end outer tube and a thrombus proximal end outer tube, and both the front blocking balloon (105) and the rear blocking balloon (504) are fitted outside the inner tubes between the thrombus distal end outer tube and the thrombus proximal end outer tube; a balloon expansion/contraction nut is fitted at the thrombus distal end outer tube, an outer end of the balloon expansion/contraction nut is statically connected with the inner tube, and an inner end of the balloon expansion/contraction nut is fitted with the thrombus distal end outer tube by threads; the front blocking balloon (105) contracts or expands as it is axially compressed or released by the thrombus distal end outer tube.

3. The ultrasonic thrombus removing system of claim 2, wherein, two ends of the front blocking balloon (105) are respectively fixedly connected with the thrombus distal end outer tube (104) and the thrombus proximal end outer tube (106) of the front sheath tube (1), and two ends of the rear blocking balloon (504) are respectively fixedly connected with the thrombus proximal end outer tube (503) and the thrombus distal end outer tube (505) of the rear sheath tube (5); frames of the front blocking balloon (105) and the rear blocking balloon (504) are mesh frames (14) that are woven from elastic metal wires, each of the mesh frames (14) is covered with a closed elastic film (15).

4. The ultrasonic thrombus removing system of claim 2, wherein, radial clearance is arranged between the core tube (502) and the inner wall of the rear sheath tube (5), several groups of convex ribs (513) are distributed in the inner tube (508) of the rear sheath tube (5), each group of convex ribs (513) comprises three or more convex ribs that are evenly distributed on an inner cylindrical surface of the inner tube (508) and parallel to an axis of the inner tube (508); a through-flow area formed by the convex ribs (513), an outer cylindrical surface of the core tube (502), and the inner cylindrical surface of the inner tube (508) is no smaller than the through-flow area of the core tube (502).

5. The ultrasonic thrombus removing system of claim 1, comprising a thrombus crushing medium supply tube, wherein the ultrasonic excitation system (8) comprises an ultrasonic generator (801), an ultrasonic transducer (802), a horn (803), and an oscillation cavity (804) that are sequentially connected, an inlet of the oscillation cavity (804) is connected with the liquid supply system (7), an outlet of the oscillation cavity (804) is connected with the thrombus breaking medium supply tube, and the thrombus crushing medium supply tube is connected with the core tube (502).

6. The ultrasonic thrombus removing system of claim 5, wherein, the oscillation cavity (804) is a cavity with a variable cross section, and is composed of a big cylindrical section (8406), a first conical reduced section (8405), a second conical reduced section (8402), a small cylindrical hole section (8403), and a horn nozzle (8404) which are arranged successively from the inlet to the outlet of the oscillation cavity (804), several groups of small through-holes (8401) are distributed in a wall surface of the cavity of the big cylindrical section (8406), each group of small through-holes (8401) is evenly distributed in a circumferential direction of the big cylindrical section (8406), an axes of the small through-holes (8401) are in a spatial helix tangent to an inner cylindrical surface (8406) of an upper oscillation cavity, with a helix angle 13 is 0-90°; a generatrix of the second conical reduced section (8402) is an arc curve; an axial length of the small cylindrical hole section (8403) is greater than an axial length of the second conical reduced section (8402) and an axial length of the horn nozzle (8404), and the axial length of the horn nozzle (8404) is smaller than an axial length of the first conical reduced section (8405).

7. The ultrasonic thrombus removing system of claim 5, wherein, the horn (803) is a unidirectional variable diameter shaft, which comprises a big cylindrical section (8301), a conical reduced section (8302) and a small cylindrical section (8303) that are arranged sequentially from outside to inside; a generatrix of the conical reduced section (8302) is a logarithmic curve.

8. The ultrasonic thrombus removing system of claim 5, wherein, the thrombus breaking medium is pulsed water, the outlet of the oscillation cavity (804) is connected with a pulsed water supply tube (6), the pulsed water supply tube (6) is connected with the core tube (502), a plurality of jet holes (512) distributed in a front end wall of the core tube (502) are arranged at a front end of the core tube (502), and the plurality of jet holes (512) form the breaker (501), the pulsed water is jetted through the breaker (501) to break the thrombus (3).

9. The ultrasonic thrombus removing system of claim 8, wherein, the plurality of jet holes (512) are arranged in a wall surface of the core tube (502) in a way that straight holes and inclined holes are arranged in separate layers in circumferences, axes of the straight holes are perpendicular to the wall surface of the core tube (502), each axis of the inclined holes and an axis of the core tube (502) form an included angle α which is 0-90°, the jet holes (512) are distributed in the wall surface of the core tube (502) at 1-20mm distance from the front end of the core tube (502), and altogether 8-20 layers of jet holes (512) are provided.

10. The ultrasonic thrombus removing system of claim 5, wherein, the liquid supply system (7) comprises a liquid supply pump (701) and a pressure/flow controller (702), wherein the liquid supply pump (701) is connected with an input end of the pressure/flow controller (702).

11. The ultrasonic thrombus removing system of claim 10, comprising a suction system (10), which comprises a suction pump (1001) and a thrombus fragment suction control device (1002) connected with the discharge tube (511) through a communicating tube (1003).

12. The ultrasonic thrombus removing system of claim 11, comprising a thrombus breaking monitoring and control device (11), a breaking zone pressure monitoring device (12), and a X-ray probe (13) arranged outside the breaking cavity (4), wherein the thrombus breaking monitoring and control device (11) is connected with the X-ray probe (13), the breaking zone pressure monitoring device (12) is a micro-pressure sensor, and the breaking zone pressure monitoring device (12) is connected between the pressure/flow controller (702) and a valve body (8407) of the oscillation cavity (804).

13. The ultrasonic thrombus removing system of claim 12, comprising a thrombus removing control CPU (9) connected with the ultrasonic generator (801), the thrombus fragment suction control device (1002), the pressure/flow controller (702), the thrombus breaking monitoring and control device (11), and the breaking zone pressure monitoring device (12) respectively.

* * * * *